United States Patent [19]
Imran et al.

[11] Patent Number: 5,908,405
[45] Date of Patent: Jun. 1, 1999

[54] LOW PROFILE BALLOON-ON-A-WIRE CATHETER WITH SHAPEABLE AND/OR DEFLECTABLE TIP AND METHOD

[75] Inventors: Mir A. Imran, Los Altos Hills; Cecily M. Hillsman; Deepak R. Ghandi, both of San Jose; Dennis L. Brooks, Windsor, all of Calif.

[73] Assignee: Intella Interventional Systems, Inc., Sunnyvale, Calif.

[21] Appl. No.: 08/876,999

[22] Filed: Jun. 16, 1997

Related U.S. Application Data

[63] Continuation of application No. 08/504,927, Jul. 20, 1995, Pat. No. 5,779,688, which is a continuation of application No. 08/331,217, Oct. 28, 1994, Pat. No. 5,520,645.

[51] Int. Cl.⁶ .................................................. A61M 31/00
[52] U.S. Cl. .............................. 604/53; 604/49; 604/95; 604/283; 606/194
[58] Field of Search ........................... 604/95–104, 280, 604/283; 606/192–194; 600/146, 152

[56] References Cited

U.S. PATENT DOCUMENTS

| | | | |
|---|---|---|---|
| Re. 35,176 | 3/1996 | Powell | 604/96 |
| 4,664,113 | 5/1987 | Frisbie et al. | 604/96 |
| 4,715,378 | 12/1987 | Pope, Jr. et al. | 128/344 |
| 4,793,305 | 12/1988 | Mar et al. | 604/96 |
| 4,838,269 | 6/1989 | Robinson et al. | 604/96 |
| 4,846,174 | 7/1989 | Willard et al. | 604/95 |
| 4,848,344 | 7/1989 | Sos et al. | 606/194 |
| 5,035,694 | 7/1991 | Kasprzyk et al. | 604/96 |
| 5,045,061 | 9/1991 | Seifert et al. | 604/96 |
| 5,069,226 | 12/1991 | Yamauchi et al. | 128/772 |
| 5,242,394 | 9/1993 | Tremulis | 604/95 |
| 5,255,690 | 10/1993 | Keith et al. | 604/96 |
| 5,338,301 | 8/1994 | Diaz et al. . | |
| 5,349,964 | 9/1994 | Imran et al. | 604/95 |
| 5,364,354 | 11/1994 | Walker et al. . | |
| 5,385,562 | 1/1995 | Adams et al. | 604/280 |
| 5,417,658 | 5/1995 | Loney et al. . | |
| 5,505,699 | 4/1996 | Forman et al. | 604/96 |
| 5,520,645 | 5/1996 | Imran et al. | 604/95 |
| 5,527,292 | 6/1996 | Adams et al. | 604/171 |
| 5,549,554 | 8/1996 | Miraki | 604/101 |
| 5,569,197 | 10/1996 | Helmus et al. | 604/96 |
| 5,613,949 | 3/1997 | Miraki . | |

*Primary Examiner*—Wynn Wood Coggins
*Assistant Examiner*—Deborah Blyveis
*Attorney, Agent, or Firm*—Harold C. Hohbach; Flehr Hohbach Test Albritton Herbert LLP

[57] ABSTRACT

A method for performing an angioplasty procedure for treating one or more stenoses in a blood vessel and branches thereof of a patient using a low profile balloon-on-a-wire catheter which has a flexible elongate tubular member with proximal and distal extremities and a removable inflation device removably secured to the proximal extremity of the flexible elongate tubular member. The method comprises the steps of inserting the balloon-on-a-wire catheter into the vessel so that the balloon is disposed in a selected stenosis in the vessel. The removable inflation device is placed on the proximal extremity of the flexible elongate tubular member so that it is in communication with the lumen in the flexible elongate tubular member. The balloon is inflated to create an enlarged flow passage through the selected stenosis. The removable inflation device is removed from the proximal extremity of the flexible elongate tubular member. A balloon catheter is introduced over the flexible elongate tubular member utilizing the flexible elongate tubular member as a stand-alone guide wire for guiding the balloon of the balloon catheter into the selected stenosis while the balloon of the balloon-on-a-wire catheter is deflated. The balloon of the balloon catheter is inflated to create a larger flow passage in the stenosis.

8 Claims, 4 Drawing Sheets

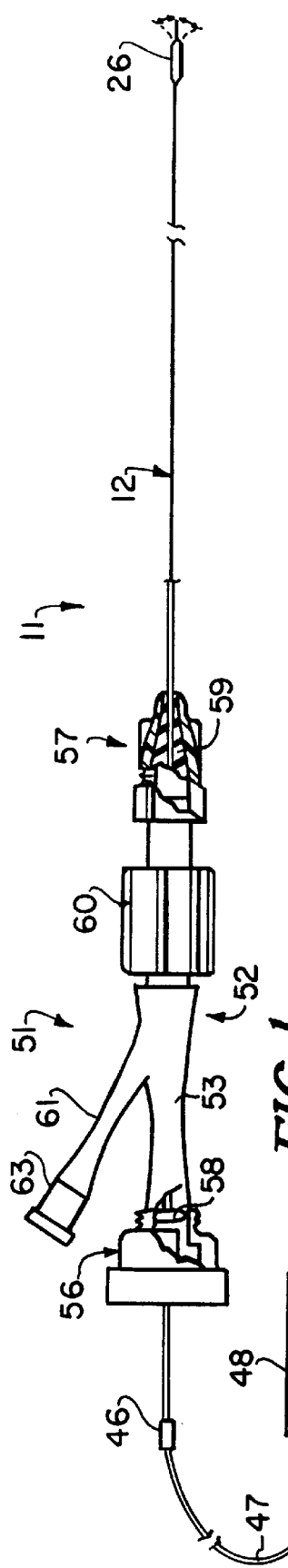
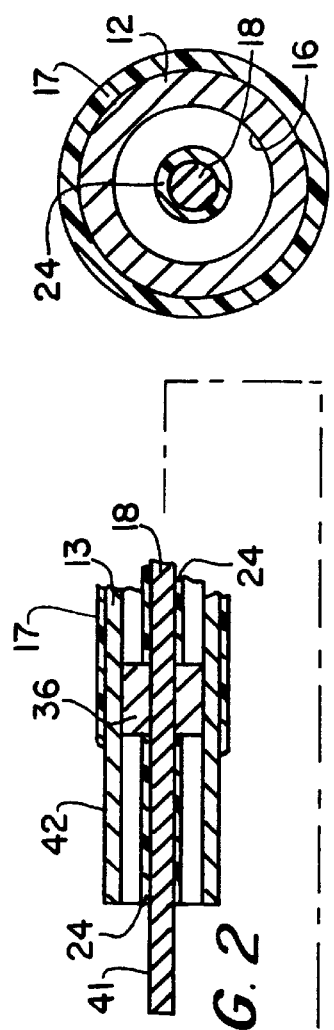
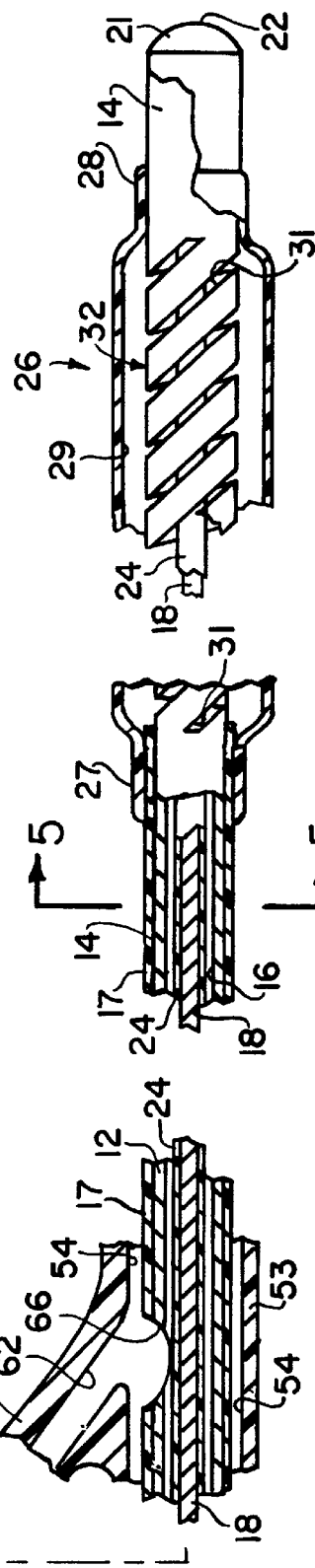
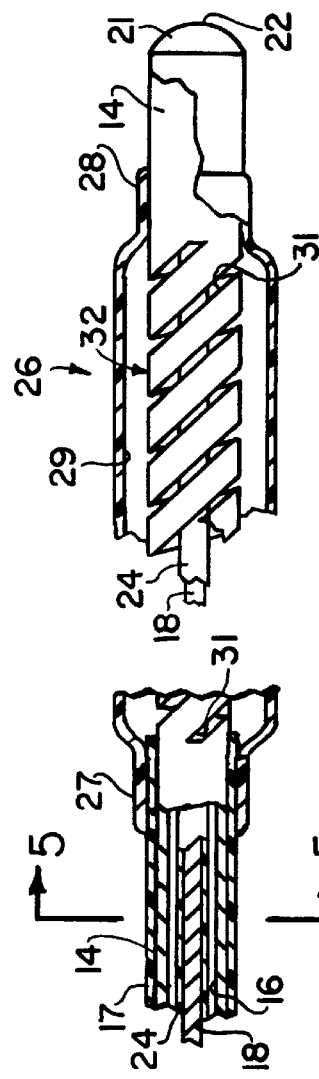
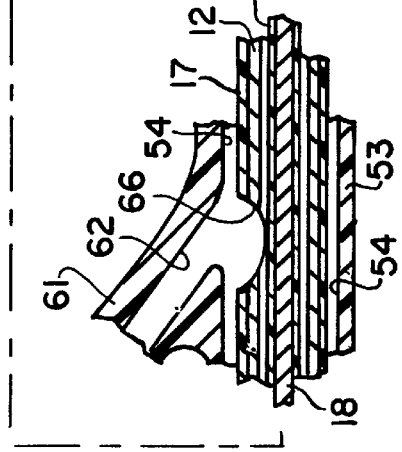

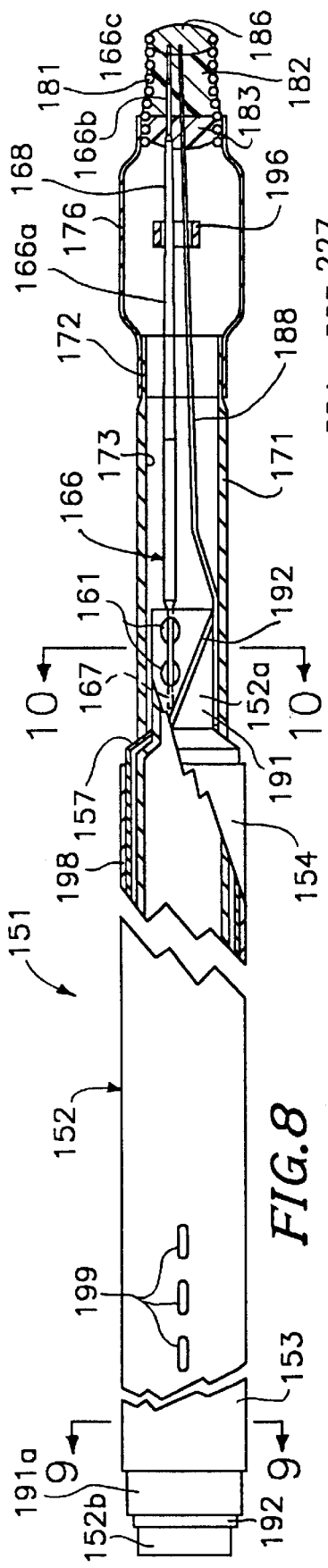
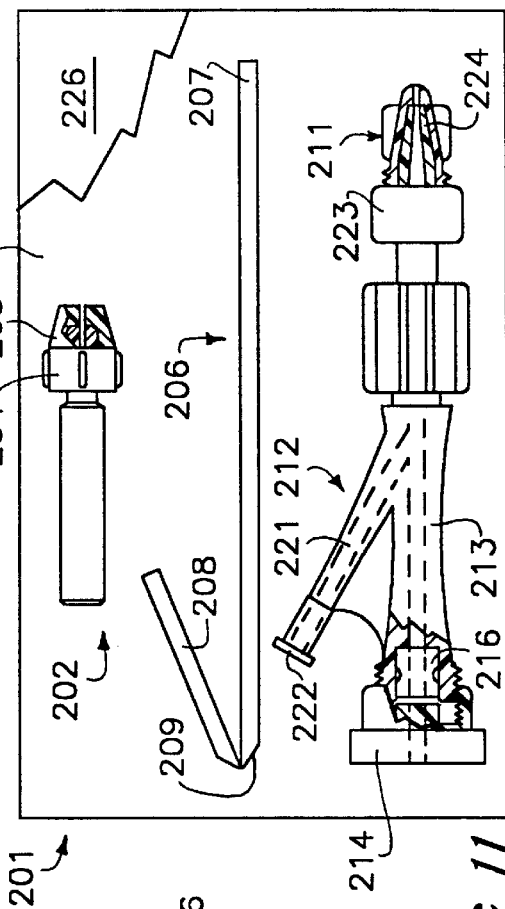
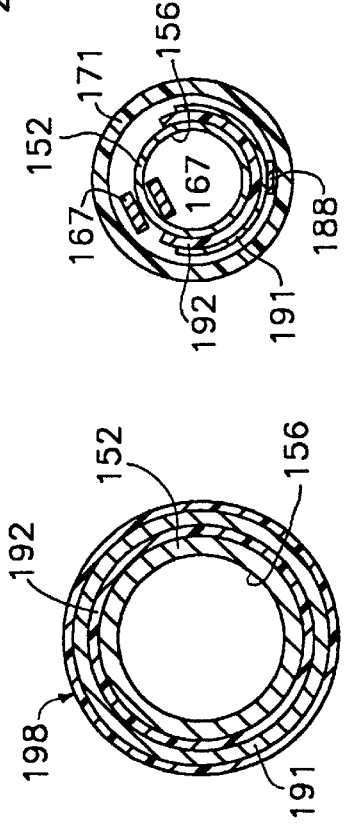
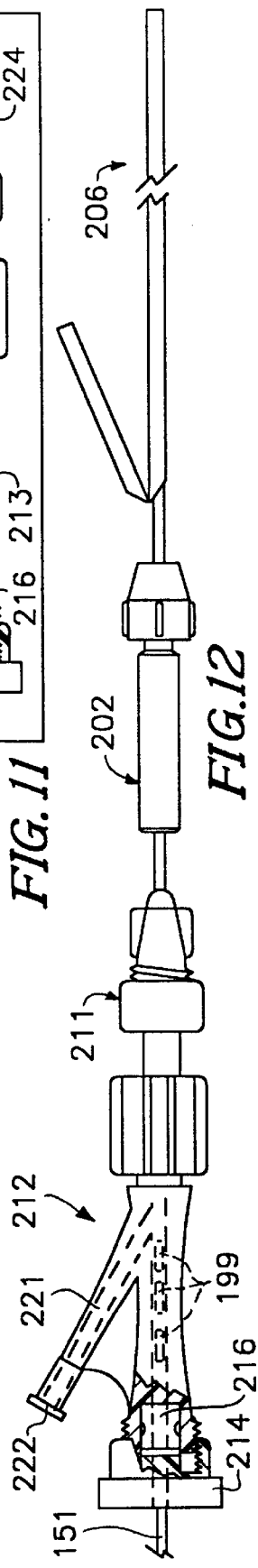
FIG.8
FIG.9
FIG.10
FIG.11
FIG.12

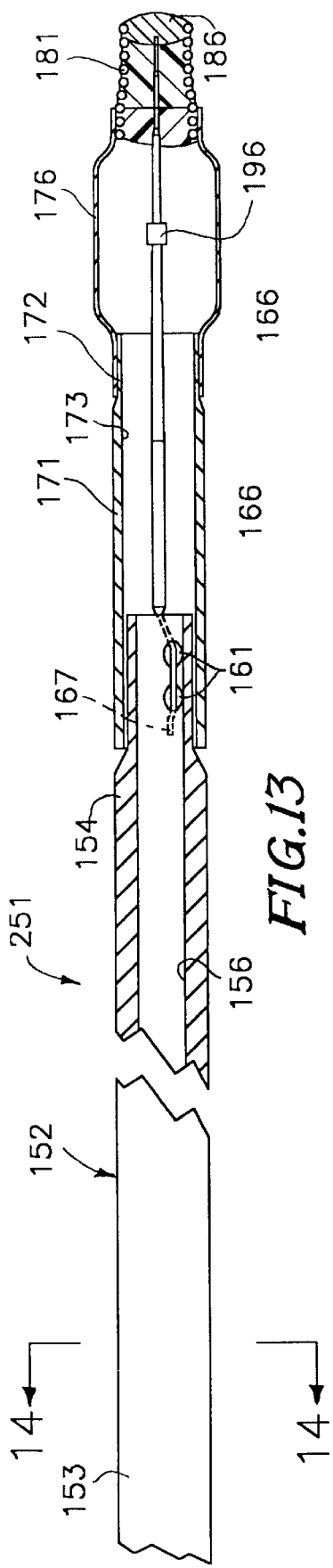
*FIG.13*
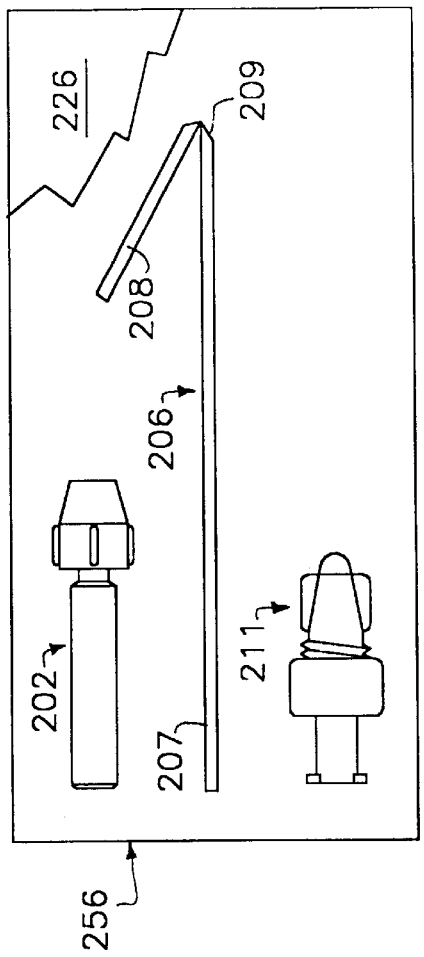
*FIG.15*
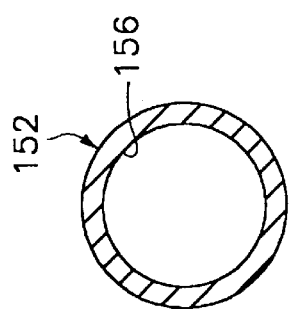
*FIG.14*
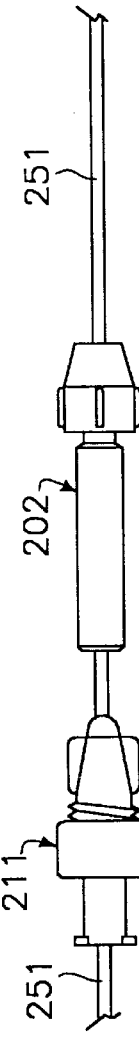
*FIG.16* ature.
LOW PROFILE BALLOON-ON-A-WIRE CATHETER WITH SHAPEABLE AND/OR DEFLECTABLE TIP AND METHOD This application is a continuation of application Ser. No. 08/504,927 filed on Jul. 20, 1995, now U.S. Pat. No. 5,799,688 which is a a continuation of application Ser. No. 08/331,217 filed on Oct. 28, 1994, U.S. Pat. No. 5,529,645.

This invention relates to a low profile angioplasty balloon-on-a-wire catheter with removable proximal attachments so that the balloon-on-a-wire catheter can be utilized as an independent guide wire for permitting larger size balloon catheters to be advanced on the balloon-on-a-wire catheter.

Balloon-on-a-wire catheters have heretofore been provided. Typically however such balloon-on-a-wire catheters have been provided with attachments on their proximal extremities which are not removable limiting the balloon-on-a-wire catheter to a single use. This requires that the balloon-on-a-wire catheter be removed if it is desired to utilize a larger size balloon during an angioplasty procedure. There is therefore need for a new and improved balloon-on-a-wire catheter which can be utilized as an independent stand-alone guide wire.

In general, it is an object of the present invention to provide a low profile balloon-on-a-wire catheter in which attachments carried by the proximal extremity can be removed so that the catheter can be utilized as an independent stand-alone guide wire.

Another object of the invention is to provide a catheter of the above character in which the distal extremity can be shaped and/or deflected.

Another object of the invention is to provide a catheter of the above character in which a removable attachment is provided on the proximal extremity of the catheter for inflating and deflating the balloon.

Another object of the invention is to provide a catheter of the above character in which an attachment is provided for making electrical connections to the proximal extremity of the catheter for steering the distal extremity of the catheter.

Another object of the invention is to provide a catheter of the above character which can be utilized as a small diameter stand-alone guide wire.

Another object of the invention is to provide a catheter of the above character in which the catheter can be utilized in a rapid exchange.

Another object of the invention is to provide a catheter of the above character which when used as an independent stand-alone guide wire so that larger size angioplasty balloon catheters can be advanced over the stand-alone guide wire.

Another object of the invention is to provide a catheter of the above character in which the balloon can be rapidly inflated and deflated.

Additional objects and features of the invention will appear from the following description in which the preferred embodiments are set forth in detail in conjunction with the accompanying drawings.

FIG. 1 is a side-elevational view of a low profile balloon-on-a-wire catheter incorporating the present invention.

FIG. 2 is an enlarged cross-sectional view of the proximal extremity of the catheter as shown in FIG. 1.

FIG. 3 is an enlarged cross-sectional view of an intermediate portion of the catheter shown in FIG. 1.

FIG. 4 is an enlarged sectional view of the distal extremity of the catheter shown in FIG. 1.

FIG. 5 is a cross-sectional view taken along the line of 5—5 of FIG. 4.

FIG. 8 is a side-elevational view partially in cross section of another embodiment of balloon-on-a-wire catheter incorporating the present invention making possible rapid inflation and deflation of the balloon and which has electrical functions.

FIG. 9 is a cross-sectional view taken along the line 9—9 of FIG. 8.

FIG. 10 is a cross-sectional view taken along the line 10—10 of FIG. 8.

FIG. 11 is a plan view of a kit including components for use with the catheter shown in FIG. 8.

FIG. 12 is a side-elevational view of the catheter shown in FIG. 8 with the accessories shown in the kit in FIG. 11 mounted on the proximal extremity of the balloon-on-a-wire catheter shown in FIG. 8.

FIG. 13 is a side-elevational view of a balloon-on-a-wire catheter incorporating another embodiment of the present invention which is of the mechanical type and does not include electrical functions.

FIG. 14 is a cross-sectional view taken along the line 14—14 of FIG. 13.

FIG. 15 is a plan view of a kit containing accessories for use with the catheter shown in FIG. 13.

FIG. 16 is a side-elevational view of the catheter shown in FIG. 13 with the accessories provided in the kit shown in FIG. 15 mounted on the proximal extremity thereof.

Figures 6, 7:
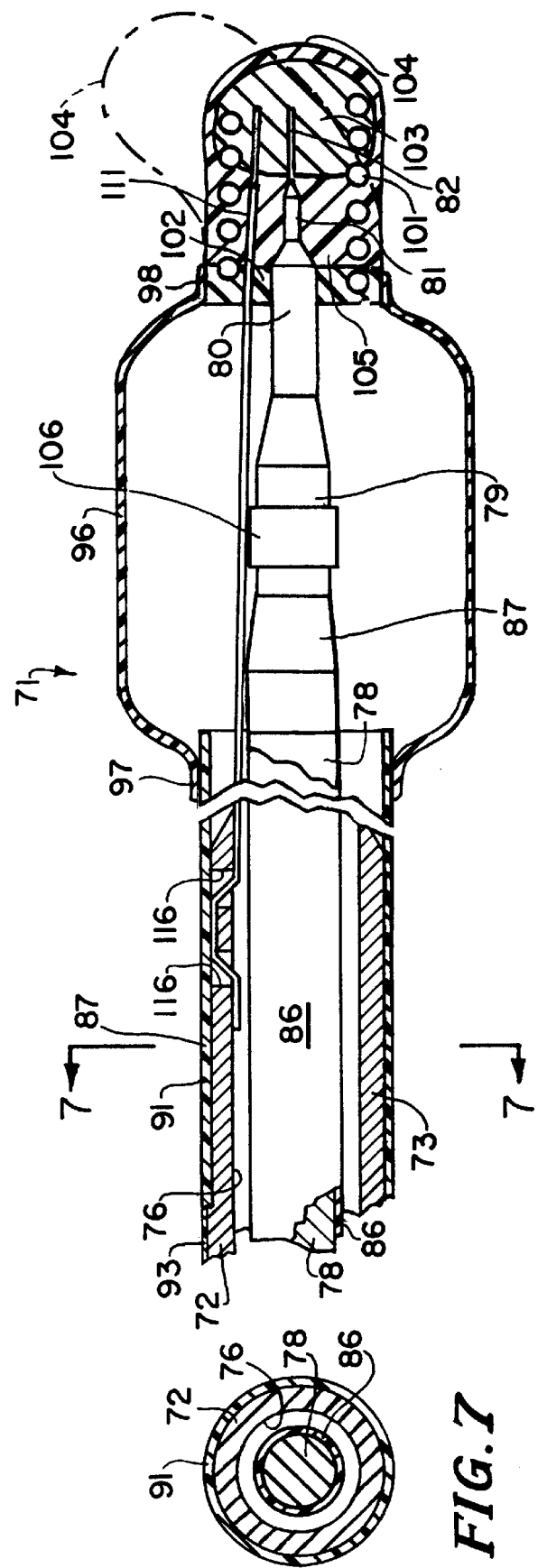
FIG. 6 is an enlarged sectional view of the distal extremity of a balloon-on-a-wire catheter incorporating another embodiment of the present invention.
FIG. 7 is a cross-sectional view taken along the line 7—7 of FIG. 6.

In general, the low profile balloon-on-a-wire catheter is comprised of a flexible elongate tubular member having proximal and distal extremities and having a lumen extending from the proximal extremity to the distal extremity. An inflatable balloon is carried by the distal extremity. Means is carried by the flexible elongate tubular member for establishing communication between the lumen and the interior of the inflatable balloon. An inflation connector is removably secured to the proximal extremity of the flexible elongate tubular member for supplying an inflation fluid to the lumen for inflating and deflating the balloon. The inflation connector when removed provides a proximal extremity for the flexible elongate tubular member which is free of obstructions so that the flexible elongate tubular member can serve as a stand-alone guide wire for permitting advancement of another balloon angioplasty catheter over the flexible elongate tubular member.

An electrical mechanism is provided in the distal extremity of the flexible elongate tubular member. Conductive means is provided in the flexible elongate tubular member and is connected to the electrical mechanism and extends to the proximal extremity. Removable connector means is coupled to the proximal extremity of the flexible elongate tubular member and makes electrical contact with the conductive means. The removable connector means when removed from the flexible elongate tubular member provides a proximal extremity on the flexible elongate tubular member which is free of obstructions so that another angioplasty catheter can be advanced over the flexible elongate tubular member utilizing the flexible elongate tubular member as a stand alone guide wire.

More in particular as shown in FIGS. 1 through 5 of the drawings, the low profile balloon-on-a-wire catheter 11 consists of a flexible elongate tubular member 12 having proximal and distal extremities 13 and 14 and having a lumen 16 extending from the proximal extremity 13 to the distal extremity 14. The flexible elongate tubular member 12 can be of a suitable material. For example it can be formed of stainless steel having an outside diameter ranging from 0.010" to 0.032" but in accordance with the present invention preferably has a size ranging from 0.014" to 0.018" in outside diameter. Such a stainless steel hypotube can have a wall thickness of 0.003" which for a 0.018" flexible elongate member would provide a lumen 16 of 0.012" in diameter. An insulating layer 17 formed of a suitable material such as a polyimide extends over the outer surface of the elongate tubular member 12.

A mandrel or core wire 18 is disposed within the lumen 16 of the flexible elongate tubular member 12 and can also be formed of a suitable material such as stainless steel or a superelastic shape memory alloy material. The core wire or mandrel 18 can have a suitable diameter such as 0.008" so that there remains a coaxial or annular space which can serve as the lumen for inflating and deflating the balloon as hereinafter described. As shown in FIGS. 1 through 5, the core wire 18 can extend from the proximal extremity to the distal extremity of the catheter 11. Typically such a mandrel or core wire 18 would have centerless ground portions of reduced diameter to impart additional flexibility to the distal extremity of the catheter as described in the embodiment of the present invention shown in FIGS. 6 and 7. The distal extremity can be flattened to provide a ribbon-like configuration which is bonded into a solder bead or weld 21 in the form of a ball to provide a hemispherical frontal surface 22. This ball 21 secures the mandrel or core wire 18 to the distal extremity of the flexible elongate tubular member 12.

In order that the mandrel or core wire 18 can be utilized as an electrical conductor, a layer of insulation 24 of a suitable material such as a polyimide of a suitable thickness as for example 0.001" is provided.

An elongate balloon 26 formed of a non-elastomeric material is bonded to the distal extremity of the flexible elongate tubular member 12. The proximal and distal extremities 27 and 28 of the balloon are bonded to the distal extremity 14 of the flexible elongate tubular member 12 by suitable means such an adhesive so that a fluid-tight seal is formed between the proximal and distal extremities 27 and 28 and the flexible elongate member 12. The balloon 26 typically would have an inflated diameter of 1.0 to 4.0 millimeters. Such a balloon would have a wall thickness range of 0.0005" to 0.002" and would have a suitable length as for example 2 to 3 centimeters.

Means is provided for establishing communication between the lumen 16 of the flexible elongate tubular member 12 and the interior 29 of the balloon 26 and consists of a spiral slot 31 extending through the wall of the hypotube forming the flexible elongate tubular member 12 as shown in FIG. 4. The slot 31 causes a helix 32 to be formed in the distal extremity of the hypotube 12. In addition to providing a means for establishing communication between the lumen 16 and the interior 29 of the balloon 26, the helix 32 serves to impart additional flexibility to the distal extremity of the flexible elongate tubular member 12 to facilitate steering and bending of the same. It should be appreciated that the helix 32 can be formed as a separate part and then be bonded by suitable means such as welding to the flexible elongate tubular member 12. Alternatively, the helix 32 can be formed in the distal extremity 14 of the flexible elongate tubular member 12. The other or proximal end of the lumen 16 is sealed in a suitable manner, such as by an epoxy seal 36 (see FIG. 2) disposed about the insulated core wire 18.

An electrical mechanism (not shown) of the type described in U.S. Pat. No. 5,238,005 and as shown in FIGS. 6 and 7 of another embodiment of the present invention utilizes a Nitinol element disposed within the helix 32 is provided for steering or bending the distal extremity 14 of the flexible elongate tubular member 12 as indicated by the dashed lines shown in FIG. 1. Conductive means is provided for supplying electrical current to the electrical mechanism and in the present embodiment of the invention this conductive means is provided by the insulated core wire or mandrel 18 serving as one conductor and the hypotube 12 forming the flexible elongate tubular member 12 serving as the second conductor to provide conductive means which extends to the proximal extremity 13. The uninsulated portion of the core wire or mandrel 18 serves to provide one cylindrical contact 41 and the uninsulated portion of the flexible elongate tubular member 12 in the form of the hypotube serves as the second cylindrical contact 42. These coaxial contacts 41 and 42 are adapted to be engaged by a conventional removable connector 46 which is connected by cable 47 to a control console 48. The control console supplies electrical power to the electrical mechanism provided in the distal extremity for causing the desired bending of the distal extremity 14 of the flexible elongate member 12. The connector 46 when removed from the proximal extremity of the flexible elongate tubular member 12 provides a proximal extremity for the flexible elongate tubular member which is free of obstructions so that another catheter can be advanced over the flexible elongate tubular member 12 permitting the flexible elongate tubular member 12 forming the catheter to be utilized as a stand alone guide wire as hereinafter described.

Removable inflation means 51 is secured to the proximal extremity of the flexible elongate member 12 and consists of a conventional Touhy-Borst wye-connector adapter 52. This adapter 52 consists of a tubular member 53 formed of suitable material such as a clear plastic which is provided with a flow passage 54 therein through which the flexible elongate tubular member 12 can extend as shown particularly in FIGS. 1 and 3. A hemostasis valve assembly 56 and a Touhy-Borst adapter 57 having respectively seals 58 and 59 thereon are provided on opposite ends of the tubular member 53 and are adapted to be moved into frictional engagement with the flexible elongate element 12 to establish fluid-tight high pressure seals therewith. A rotating Luer connection having a rotatable sleeve 60 interconnects the wye connector 52 and the Touhy-Borst adapter 57 and can be used as a means for applying torque. It is adapted to be engaged by the fingers of the hand for rotating the distal extremity of the catheter and/or guide wire 12. The proximal seal assembly 56 is loosened slightly to permit rotation of the flexible elongate tubular member within the seal 58 while retaining a fluid-tight seal therewith.

The tubular member 53 is provided with a leg 61 which branches off at an angle from the flow passage 54. It is provided with a flow passage 62 in communication with the flow passage 54 and in communication with the conventional Luer fitting 63 which is adapted to receive an inflation device (not shown) that can be utilized for introducing an inflation fluid in the form of a radiopaque dye or a saline solution into the passage 62 and into the passage 54 so that the inflating fluid can be introduced into the lumen 16 of the flexible elongate member 12. Means is provided for establishing communication between the passage 54 and the lumen 16 of the flexible elongate tubular member and consists of one or more elongate slots 66 formed in the sidewall of the hypotube forming the flexible elongate tubular member 12.

It can be seen that the inflation means 51 can be readily removed from the proximal extremity of the flexible elongate tubular member 12 by releasing the seals 58 and 59 from the flexible elongate tubular member 12 and then slipping the hemostatis valve 56, the wye-connector 52 and the Touhy-Borst adapter 57 off of the proximal extremity of the flexible elongate tubular member 12 to provide a proximal extremity on the flexible elongate tubular member 12 which is free of obstructions so that another angioplasty catheter can be advanced over the flexible elongate tubular member utilizing the flexible elongate tubular member as a stand alone guide wire.

In connection with the present invention it should be appreciated that the core wire or mandrel if desired can be provided of a reduced length as for an example extending only approximately 30 centimeters from the distal extremity of the catheter 11 typically having a length of 150 to 180 centimeters. In such an embodiment, the conductive means would take the form of at least one additional wire and possibly two additional wires connected to the electrical mechanism in the distal extremity of the flexible elongate tubular member 12 and extending to the proximal extremity where they can be secured to conductive slip rings (not shown) to form the electrical connection with the connector 46.

Operation and use of the low profile balloon-on-a-wire catheter may now be described as follows. Let it be assumed that an angioplasty procedure is to be performed on a patient who has one or more stenoses or occlusions in an arterial vessel and branches thereof which restrict blood flow therethrough. For that reason it normally is desirable to utilize a very low profile balloon-on-a-wire catheter such as disclosed in the present invention. Before commencement of the procedure, the inflation adapter 51 and the connector 46 would typically be placed on the proximal extremity of the catheter 11. A guiding catheter (not shown) is introduced into the femoral artery in a conventional manner after which the low profile balloon-on-a-wire catheter 11 incorporating the present invention is introduced into the guiding catheter and then into the vessel by steering the same by use of the hereinbefore described electrical mechanism and/or with the use of the rotatable sleeve 60 through any tortuosities which may be encountered in the vessel until the selected stenosis is reached. The progress of the distal extremity of the low profile balloon-on-a-wire catheter can be observed fluoroscopically in a manner well known to those skilled in the art. The catheter 11 is then advanced through the selected stenosis until the balloon 26 is in registration with the selected stenosis.

After the balloon 26 has been positioned within the selected stenosis, the balloon 26 can be inflated by supplying an inflation fluid as for example by an inflation device to the adapter 51 so that the fluid will pass to the lumen 16 of the flexible elongate member 12 and then in to the interior 29 of the balloon 26. The balloon 26 can be inflated and deflated one or more times as desired by the physician to create an opening in the selected stenosis which is at least large enough to permit some blood to flow through the selected stenosis.

Let it be assumed that it is desired to still further expand the opening through the selected stenosis by the use of an over-the-wire catheter of a conventional type having a larger size balloon. When this is to be done, the connector 46 is removed and the balloon 26 is deflated after which the adapter 51 is removed by slipping it off of the proximal extremity of the flexible elongate member 12. This can be readily accomplished by merely loosening the seals 56 and 57 from the elongate tubular member 12 and slipping it off of the flexible elongate member 12.

The catheter 11 which remains in place has a distal extremity with an outside diameter approximately that of the main body of the catheter. Thus, in the embodiment shown in FIGS. 1–5 the balloon 26 when deflated would only have a nominal wall thickness of 0.0003"–0.0005" so that when the balloon 26 is deflated the distal extremity of the catheter has an overall diameter which is approximately equal to or less than the diameter of the catheter 11 as for example 0.018". A conventional balloon catheter can then be introduced over the catheter 11 utilizing the catheter 11 as a stand-alone guide wire to guide the larger size balloon angioplasty catheter into the selected stenosis. If desired, the catheter 11 of the present invention can be left in a position with the deflated balloon 26 thereon in registration with the selected stenosis. The other balloon of the conventional angioplasty catheter then can be moved over the deflated balloon 26. Alternatively, the catheter 11 with the deflated balloon 26 thereon can be advanced distally beyond the selected stenosis. The conventional balloon catheter can then be advanced over the catheter 11 until its balloon is in registration with the selected stenosis. The balloon carried by the conventional balloon catheter can then be inflated and deflated one or more times as desired by the physician to additionally dilate the selected stenosis to thereby create increased blood flow through the selected stenosis. If desired, the conventional angioplasty catheter can be removed leaving the catheter and/or guide wire 11 or catheter/guide wire of the present invention still in place and then advancing a still larger size conventional balloon catheter over the catheter 11 and utilizing the same inflation and deflation procedure until the desired dilation of the stenosis has been obtained.

The larger size balloon catheter can then be removed along with the catheter/guide wire 11 of the present invention. Alternatively, if it is desired to treat another stenosis in a branch of the same arterial vessel, the catheter or guide wire 11 of the present invention can be left in place and thereafter advanced or positioned so that the balloon 26 is in registration with the another selected stenosis. The inflation adapter 51 is then remounted on the proximal extremity of the flexible elongate tubular member 12 and the seals 56 and 57 fastened. The balloon 26 can then be inflated to enlarge the flow passage through the another selected stenosis in the same manner as for the selected stenosis. The inflation adapter 51 can then be removed to permit other balloon catheters to be advanced over the free-of-obstructions proximal end of the catheter 11 in the manner hereinbefore described to provide the desired flow passage through the another selected stenosis. The same procedure can be used in another selected stenosis which may be present in other branches of the arterial vessel of the patient. After all of the stenoses have been treated, the catheter 11 can be removed and the entry site can be closed.

In connection with the use of the catheter 11 of the present invention, it should be appreciated that a conventional rapid exchange catheter can be utilized in connection with the catheter 11 if desired.

Another embodiment of a low profile balloon-on-a-wire catheter incorporating the present invention is disclosed in FIGS. 6 and 7. The balloon-on-a-wire catheter 71 shown therein consists of a flexible elongate tubular member 72 which has a proximal extremity (not shown) and a distal extremity 73. The flexible elongate tubular member 72 can be formed of a suitable material such as a stainless steel hypotube having an outside diameter of 0.018" and having a wall thickness of 0.002" to provide a balloon inflation lumen 76 extending from the proximal extremity (not shown) to the distal extremity 73. A core wire or mandrel 78 is disposed within the lumen 76 and is formed of a suitable material such as stainless steel. It can be of a suitable diameter as for example 0.006" to 0.008". The distal extremity of the core wire or mandrel 78 is provided with a portion 79 of reduced or smaller diameter as for example 0.004", another portion 80 of a still smaller diameter as for example 0.003", or portion 81 of a diameter of 0.002" and a flattened rectangular ribbon-like portion 82. The core wire 78 is coated with an insulating coating 86 of a suitable material such as a polyimide to a thickness of approximately 0.0005". The distal extremity of the flexible elongate tubular member 72 is ground down to form an annular recess at 87.

A sleeve or elongate tubular member 91 is provided which extends for a distance of 25–27 cm from the distal extremity of the hypotube 72 and is formed of a suitable material such as a polyimide. It has an outside diameter as for example of 0.018" and a wall thickness of 0.0015" to 0.004" and preferably an insulating layer 93 formed of a polyimide coating covers the entire length of the hypotube or flexible elongate member 72.

A balloon 96 formed of a typical non-elastomeric material such as polyethylene or PET has its proximal extremity 97 bonded to the exterior of the sleeve 91 by suitable means such as a heat seal. The distal extremity 98 of the balloon 96 is also bonded to the proximal end of a coil 101 by suitable means such as a heat fuse or seal. The spring 101 is formed of a radiopaque suitable material such as a platinum tungsten alloy. Its proximal extremity is sealed to the core mandrel by suitable means such as an adhesive 102. The distal extremity of the coil spring 101 is secured to the core wire or mandrel 78 by a TEG weld forming a ball 103 providing a hemispheric forwardly or distally facing surface 104. The adhesive 102 bonds the coil 101 to core wire or mandrel 78 and a polymer 105 such as silicone fills the space between the adhesive 102 and the ball 103. The silicone also encapsulates the ball 103, which is first encapsulated by a uv-curable adhesive. A radiopaque marker 106 formed of a suitable material such as gold or platinum is disposed within the interior of the balloon 96 equidistant from the ends thereof on the exterior surface of the insulating coating 86 on the core mandrel 78.

Suitable steering means of the type disclosed in U.S. Pat. No. 5,238,005 is provided to permit steering of the distal extremity of the catheter or guide wire 71 as shown by dotted lines in FIG. 6 of the coil spring 101. This steering means consists of a Nitinol actuator wire or ribbon 111 having one end embedded in the ball 103 and having the other end secured to the distal extremity of the flexible elongate tubular member 72 by suitable means such as by bending said other end to extend through a pair of retaining slots 116 in the flexible elongate tubular member 72 and being retained therein by the sleeve 91 as shown in FIG. 6. The conductive means for supplying electrical energy to the steering means in the form of the Nitinol wire 111 is provided by the insulated stainless steel core wire or mandrel 78 serving as one of the insulated conductors and the hypotube forming the flexible elongate tubular member 72 serving as the other conductor. Alternatively, first and second insulated conductive wires can be provided within the balloon inflation lumen 76 to provide such conductive means.

The proximal extremity of the catheter and/or guide wire 71 shown in FIGS. 6 and 7 is constructed in a manner very similar to that shown in the previous embodiment and therefore will not be described in detail.

The operation and use of the catheter shown in FIGS. 6 and 7 is substantially identical to that described in connection with the previous embodiment.

It is apparent from the foregoing that there has been provided a low profile balloon-on-a-wire catheter which can be converted from a catheter to a guide wire so that additional conventional balloon catheters can be introduced over the balloon-on-a-wire catheter utilizing the catheter as a stand-alone guide wire. The conversion from a catheter to a guide wire can be readily accomplished merely by removing the attachments provided on the proximal extremity of the catheter, namely the attachment for inflating and deflating the balloon and the connector for making electrical connections to the electrical steering means. The catheter or guide wire is one which when converted can be utilized with rapid exchange catheters.

In the event it is desired to provide a balloon-on-a-wire angioplasty catheter of the type hereinbefore described which has more rapid inflation and deflation times, a balloon-on-a-wire catheter construction of the type as shown in FIGS. 8, 9 and 10 can be utilized. The balloon-on-a-wire catheter 151 incorporating the present invention as shown in FIG. 8 consists of a flexible elongate tubular member 152 having proximal and distal extremities 153 and 154. The flexible elongate tubular member 152 can be formed of a suitable material such as stainless steel. However, in order to provide additional torquability and additional resistance to kinking, it has been found desirable to utilize a shape memory alloy such as a nickel titanium alloy that has superelastic capabilities inhibiting the tubular member 152 from taking a permanent set. The flexible elongate tubular member 152, which also can be called a hypo tube, can have a preferred inside diameter as for example 0.010" and an outside diameter of 0.017" to provide a wall thickness of 0.0035". It can have a suitable length, as for example 150–170 centimeters, which is conventional for angioplasty catheters. Thus, with a hypotube 152 of this size and length, a balloon inflation lumen 156 is provided which has a diameter of 0.010" to 0.0125". The distal extremity 154 is provided with a taper 157 which adjoins a centerless ground portion 152a that is provided with a plurality of longitudinally extending spaced-apart slots 161.

A core mandrel 166 is provided having a proximal extremity 167 of a suitable diameter such as 0.004" that is threaded into and locked into the spaced-apart slots 161. The core mandrel 166 is provided with a distal extremity 168 and with a portion 166a that is tapered and adjoins a portion 166b having a smaller diameter and a flattened portion 166c adjoining portion 166b. The core mandrel 166 can have a suitable length as for example 30 centimeters and can have a suitable diameter as for example 0.005"–0.012". The core mandrel 166 can be formed of a suitable material such as stainless steel or a nickel titanium alloy. An outer sleeve 171 formed of a suitable insulating material such as a polyimide having an outside diameter of 0.018" and an inside diameter of 0.0165" is secured to the portion 152a by suitable means such as an adhesive. Its distal extremity is provided with an annular recess 172 having one end of a balloon 176 typically formed of a non-elastomeric material such as PET secured in the annular recess 172 by suitable means such as a heat fuse or seal. The other end of the balloon 176 is bonded to the coil spring 181 typically formed of a suitable radiopaque material such as platinum, or a platinum tungsten alloy by suitable means such as a heat fuse or seal. The coil 181 is encapsulated in a suitable material such as a silicone 182 to provide an air-tight seal for the balloon 176 and to inhibit heat loss. In addition, an adhesive 183 is placed in the coil 181 adjacent the distal extremity of the balloon 176 and forms an air-tight and fluid-tight seal with respect to the distal extremity of the balloon. A TEG or plasma weld 186 is provided on the distal extremity of the coil spring 181 and is bonded to the distal extremity of the core mandrel 166 as shown in FIG. 8 to form one electrical connection for supplying energy to an actuator member 188 having one end connected into the TEG weld 186.

The actuator member 188 is formed of a suitable material such as a nickel titanium alloy having a negative coefficient of expansion. It is insulated so that it does not make contact with the conductive core mandrel 166. The actuator member 188 extends proximally and makes contact with and is connected to a conductive coating 191 formed of a suitable material such as silver. The conductive coating 191 is carried by an insulating layer 192 formed of a suitable material such as a polyimide which overlies the exterior of the hypotube 152. A marker band 196 is provided on the core mandrel 166 and extends over the actuator member 188 and is formed of a suitable radiopaque material. The band 196 is disposed equidistant between the ends of the balloon 176 and is used to visualize the deployment of the balloon 176 during use.

The conductive coating 191 extends to the proximal extremity 153 and is covered with an insulating coating 198 having lubricous characteristics. The coating 198 stops short of the proximal extremity of the conductive coating 191 carried by the insulating layer 192 so that it is exposed at 191a for making electrical contact therewith in the manner hereinbefore described.

The proximal extremity of the hypotube 152 is provided with a plurality of longitudinally extending spaced-apart slots 199 disposed in the side wall. The slots 199 can have a suitable size as for example they can be rectangular having a length ranging from 0.029" to 0.031" and having a width of 0.01" and can be spaced apart by suitable distance as for example 0.1". The slots 199 are utilized for providing inflation ports giving access to the bore or central lumen 156 for inflating and deflating the balloon 176. In addition to the inflation slots 199 being accessible at the proximal extremity of the catheter 151, first and second electrical connections for supplying energy to the actuator member 188 are also accessible from the proximal extremity with the first electrical connection being provided by the exposed portion 152b of the flexible elongate tubular member or hypotube 152 and the second electrical connection by the exposed portion 191a of the conductive layer 191.

The catheter 151 shown in FIG. 8 can be supplied in this form to the prospective user without any proximal attachments, which can be supplied in a kit 201 of the type shown in FIG. 11. The kit 201 includes a torquer 202 of a conventional type which is provided with a collet 203. Rather than being formed of brass as in a conventional torquer, the collet 203 is formed of plastic so that it will not damage the outer coating 198 when the catheter 151 shown in FIG. 8 is disposed within the torquer 202. The kit 201 in FIG. 11 also includes a splittable introducer 206 of a conventional type which typically is in the form of plastic and which is provided with a working length 207 which has a bent-over proximal extremity 208 which can serve as a handle. It can have a suitable length, as for example 10–15 centimeters and is provided with an inlet opening 209 leading to a passage (not shown) extending through the introducer through which the catheter 151 can be introduced. The introducer 206 is adapted to be used to facilitate introducing the catheter 151 of the present invention into a guiding catheter conventionally used in angioplasty procedures in a manner well known to those skilled in the art. The kit 201 also includes a Touhy-Borst adapter 211 which is removably mounted on the distal extremity of a Y-adapter 212 also of a conventional type. The Touhy-Borst adapter 211 is provided with a threaded cap 223 which engages a sealing member 224 that forms a high-pressure seal.

The Y-adapter 212 is provided with a main or central arm 213 which carries a rotatable threaded cap 214 adapted to compress a sealing member 216 carried by the central arm 213 to form a high-pressure seal with respect to the catheter 151. The Y-adapter 212 is also provided with a side arm 221 carrying a Luer-type fitting 222 that is adapted to be connected to an inflation device (not shown) of a conventional type which can be connected to the side arm 221 for inflating and deflating the balloon 176. The attachments or accessories 202, 206, 211 and 212 are relatively inexpensive and can be readily packaged into the kit by mounting them on a cardboard 226 and covering them with plastic shrink wrap 227 in a conventional manner.

Operation and use of the catheter 151 may now be briefly described as follows. Let it be assumed that an angioplasty procedure of the type hereinbefore described is to be performed on a patient who has a stenosis or an occlusion at least partially blocking a vessel carrying blood. The catheter 151 is prepared by taking the catheter which has been packaged in an appropriate manner and separating it from the package and then taking the kit 201 and opening the same. The torquer 202 is first taken and advanced over the proximal extremity of the catheter 151 so that it is distal of the slots 199. The collar 204 is then rotated to engage the collet 203 to cause the collet 203 to firmly grasp the surface of the catheter 151 so that the catheter 151 can be rotated by use of the torquer 202. Thereafter, the Touhy-Borst adapter 211 which is removably attached to the Y-adapter 212 is advanced over the proximal extremity 153 of the catheter 151 so that the Touhy-Borst adapter 211 is proximal of the torquer 202 and is distal of the slots 199 but with the threaded cap 214 of Y-adapter 212 being proximal of the slots 199. The threaded cap 223 on the Touhy-Borst adapter 211 can then be adjusted to engage the sealing member 224 to compress the same to form a high-pressure seal between the Touhy-Borst adapter 211 and the catheter 151. Thereafter, the threaded cap 214 on the Y-adapter 212 can be rotated to also compress the seal 216 to form a high-pressure seal between the Y-adapter 212 and the catheter 151. Thus it can be seen that high pressure seals are provided on opposite sides of the slots 199.

After the catheter 151 has been prepared for use, a guiding catheter (not shown) is introduced into a femoral artery of the patient in a conventional manner. The introducer 206 then can be placed in the guiding catheter. The distal extremity of the catheter 151 is then advanced into the opening 209 of the introducer 206 which guides the catheter 151 into the guiding catheter after which it can be advanced through the guiding catheter and into the desired vessel. The physician observes advancement of the same by fluoroscopy, observing the advancement of the marker 196 and coil 181. The torquer 202 is utilized to facilitate maneuvering in tortuous vessels. As the catheter 151 is being advanced, the distal extremity can be bent in a desired direction by use of a control console of the type hereinbefore described for causing a bend to be placed into the distal extremity of the catheter by supplying electrical energy to the actuator member 188 in a manner hereinbefore described.

After the deflated balloon 176 has been advanced into the desired position in the stenosis to be treated, an inflation device (not shown) of a conventional type is attached to the side arm 221 and the balloon is rapidly inflated to its maximum size to a pressure of at least 10 atmospheres and preferably at least 15–20 atmospheres. This inflation can occur very rapidly even though the catheter 151 is of a very small size because the large lumen 156 which is provided opens into the large flow passage 173 provided in the outer sleeve 171 and is in direct communication with the interior of the balloon 176. Such a large inflation lumen 156 is made possible because with the construction herein disclosed, it is unnecessary for the core wire or mandrel 166 to extend through the flexible elongate tubular member or hypotube 152 to the proximal extremity thereby providing a large inflation lumen extending from the proximal extremity 153 of the catheter to the flow passage 173 provided in the outer sleeve 171. Thus in the present invention, the core mandrel 166 is only present in the distalmost extremity of the catheter 151.

The balloon 176 can also be deflated in a very short period of time, as for example six seconds. These rapid inflation/deflation times have been provided without compromising the capabilities of the catheter 151. The distal extremity can be shaped and deflected in the manner hereinbefore described. It also has the torquability and feel that is substantially equivalent to that of a High-Torque Floppy manufactured by Advanced Cardiovascular Systems, Inc. The desired torquability is retained by the use of the flexible elongate tubular member or hypotube 152 having increased wall thickness and being formed of superelastic material.

Another embodiment of a low profile angioplasty balloon-on-a-wire catheter with shapable and/or deflectable tip is shown in FIGS. 13 and 14 and is of the mechanical type and does not include the electrical functions provided by the catheter 151 shown in FIGS. 8–10. Thus, the catheter 251 shown in FIGS. 13 and 14 consists of a flexible elongate member 152 of the type hereinbefore described in connection with the embodiment shown in FIGS. 8–10. Thus in the same manner as in the embodiment shown in FIGS. 8—10, there is provided an outer sleeve 171. A balloon 176 is carried thereby with a core mandrel 166 extending from the distal extremity of the flexible elongate tubular member 152 and is secured to the TEG weld 186. The principal difference between the two embodiments of the invention shown in FIGS. 8–10 and that shown in FIGS. 13–14 is that the need for providing electrical conductors for supplying energy to an actuator member has been eliminated since the actuator member has been eliminated. Thus, the need for insulating coatings has been eliminated. The catheter 251 shown in FIG. 13 can be supplied to the customer without any fittings or attachments being provided on the proximal extremity. The necessary fittings or accessories can be supplied in a kit 256 which in many respects is similar to the kit 201. It is provided with a torquer 202, a splittable introducer 206 and a Touhy-Borst adapter 211 of the type hereinbefore described with the exception that the torquer 202 rather than being provided with a plastic collet is provided with a conventional metal collet since the collet is to engage the metal surface of the flexible elongate tubular member 152. These attachments or accessors 202, 206 and 211 can be packaged in the same manner as the kit 201.

Operation and use of the catheter 251 may now be briefly described as follows. Its operation and use is very similar to the catheter 151 hereinbefore described, although its operation and use is simpler because of the elimination of electrical features and providing solely mechanical features. Assuming that a similar angioplasty procedure is to be performed, the catheter 251 can be prepared by opening the kit 256 and placing the torquer 202 over the proximal extremity and tightening it on the catheter distal of the proximal extremity 153. The Touhy-Borst adapter 211 can be mounted on the proximal most portion of the proximal extremity 153 since the balloon inflation lumen 156 opens through the proximal extremity 153. The Touhy-Borst adapter is then adjusted to provide a high-pressure seal between the Touhy-Borst adapter and the proximal extremity 153 of the catheter 251. A conventional inflation device can then be secured directly to the Touhy-Borst adapter 211. The distal extremity of the catheter 251 can then be shaped if desired by the physician by utilizing the fingers of the hand to bend the distal extremity of the catheter 251, in particular the core mandrel 166 in a manner well known to those skilled in the art in utilizing angioplasty guide wires to place a predetermined bend in the distal extremity on the balloon-on-a-wire catheter 251. It thereafter can be introduced into the introducer 206 and into the guiding catheter and advanced into the desired location utilizing the torquer 202 while observing the advancement fluoroscopically by viewing the radiopaque marker 196 and coil 181. As soon as the balloon has been advanced into the stenosis, the balloon can be readily inflated and deflated by use of the inflation device connected to the Touhy-Borst adapter 211. Rapid inflation and deflation to at least 10 atmospheres is possible because of the large size of the lumen 156 in comparison to the size of the catheter 251. As explained previously, this is made possible by eliminating the use of a core wire within the passage or lumen 156 and only providing the core wire or mandrel 166 at the distal extremity of the catheter. The balloon inflation-deflation lumen in the flexible elongate tubular member is free of obstructions and is the only lumen in the flexible elongate tubular member and includes substantially the entire cross-sectional area within the flexible elongate tubular member.

In the event it is desired to reach the site of the passage through the stenosis by a larger balloon, the Touhy-Borst adapter 211 and the torquer 202 can be removed from the proximal extremity. The splittable introducer 206 can be removed by grasping the bent-over portion 208 with the hand and pulling it sidewise to split off the catheter shaft provided by the flexible elongate tubular member 152. A conventional balloon catheter having a larger balloon then can be advanced over the catheter 251 utilizing the catheter 251 as stand-alone guide wire for the larger size balloon angioplasty catheter. Thus, while the balloon-on-a-wire catheter 251 is still in place, the other balloon catheter can be advanced over the balloon-on-a-wire catheter using it as a stand-alone guide wire until its balloon is positioned within the stenosis after which that balloon can be inflated by a conventional inflation-deflation device. The conventional balloon catheter can be advanced over the deflated balloon of the balloon-on-a-wire catheter while the balloon of the balloon-on-a-wire catheter is still in place in the stenosis. Alternatively, the deflated balloon of the balloon-on-a-wire catheter can be advanced so that it is distal of the stenosis after which the balloon of the conventional balloon catheter can be advanced into the stenosis and inflated.

If a still larger balloon is needed, the balloon catheter being utilized can be removed over the balloon-on-a-wire catheter 251 and another conventional balloon catheter inserted over the proximal extremity and advanced into the stenosis and inflated and deflated until the appropriate size flow passage or passageway has been formed in the stenosis. Thereafter, the conventional balloon catheter along with the balloon-on-a-wire catheter 251 can be removed in unison or separately if desired.

Thus, it can be seen that the balloon-on-a-wire catheter of the present invention can be utilized because of its small diameter to form an initial passageway in the stenosis and can be left in place and additional balloon catheters of various sizes can be advanced over the same utilizing it as a stand-alone guide wire to advance the balloon carried thereby into registration with the stenosis and performing the appropriate inflation and deflation of the balloon carried thereby. The balloon-on-a-wire catheter of the present invention, in addition to performing dilation of the stenosis as hereinbefore described, also serves as a stand-alone guide wire for advancement of other larger size conventional balloon catheters into the stenosis without removal of the balloon-on-a-wire catheter 251. The balloon-on-a-wire catheter 251 is removed only once during an angioplasty procedure. The use of the kit for the proximal attachment parts for the balloon-on-a-wire catheter greatly reduces the cost of the balloon-on-a-wire catheter and makes it possible to readily attach and detach the necessary parts to the proximal extremities of the balloon-on-a-wire catheters. The balloon-on-a-wire catheter 151 hereinbefore described having electrical characteristics can be utilized in a similar manner as a stand-alone guide wire merely by removing the Y-adapter 212, the Touhy-Borst adapter 211, the torquer 202 and the splittable introducer 206.

In connection with the present invention, it can be seen that the balloon-on-a-wire catheter of the present invention can be supplied to a prospective user in which its proximal extremity is free of obstructions and has a lumen which is accessible at the proximal extremity. A kit along with one or more balloon catheters of a conventional type of various balloon sizes can be shipped at the same time to the prospective user. The kit includes the necessary accessories for operating the balloon-on-a-wire catheter while still permitting the balloon-on-a-wire catheter to be utilized as a stand-alone guide wire for the other conventional balloon catheter as hereinbefore explained. The kit need only contain those attachments or accessories which are necessary to complete the functions of the balloon-on-a-wire catheter. Thus as hereinbefore explained, the kit can include removable inflation means which for the mechanical type balloon-on-a-wire catheter need only provide one high pressure seal or with respect to the balloon-on-a-wire catheter having electrical functions having inflation means capable of providing first and second high pressure seals disposed on opposite ends of the side opening in communication with the inflation-deflation lumen. The kit can also include an introducer to facilitate introduction of the balloon-on-a-wire catheter into the guiding catheter conventionally used in angioplasty procedures. The cost of manufacture of the balloon-on-a-wire catheter of the present invention is reduced substantially with the attachments or accessories being supplied in a separate kit.

We claim:

1. A method for performing an angioplasty procedure to enlarge a flow passage in a stenosis in a blood vessel of a patient by the use of a low profile balloon-on-a-wire catheter having a flexible elongate tubular member with proximal and distal extremities and with a balloon inflation-deflation lumen extending from the proximal extremity to the distal extremity, an inflatable balloon carried by the distal extremity of the flexible elongate tubular member, means carried by the flexible elongate tubular member for establishing communication between the lumen and the interior of the balloon and removable inflation means removably secured to the proximal extremity of the flexible elongate tubular member for supplying an inflation fluid to the lumen for inflating and deflating the balloon, said flexible elongate tubular member having a side opening therein in the proximal extremity thereof in communication with the lumen, said removable inflation means including first and second high pressure seals disposed on opposite sides of the side opening so that that inflation fluid from the removable inflation means must pass through said side opening, the method comprising the steps of inserting the balloon-on-a-wire catheter into the vessel so that the balloon is disposed in the stenosis in the vessel, placing the removable inflation means on the proximal extremity of the flexible elongate tubular member so that the first and second high pressure seals are disposed on opposite sides of the side opening, inflating the balloon through the removable inflation means to a pressure of at least ten atmospheres to create an enlarged flow passage through the stenosis, deflating the balloon, removing the removable inflation means removably secured to the proximal extremity of the flexible elongate tubular member to provide a proximal extremity of the flexible elongate tubular member which has an outer cylindrical surface which is free of obstructions and having the side opening therein, introducing a balloon catheter over the proximal extremity of the flexible elongate tubular member which is free of obstructions, utilizing the flexible elongate tubular member as a stand-alone guide wire for guiding the balloon of the balloon catheter into the stenosis while the balloon on the balloon-on-a-wire catheter is deflated, inflating the balloon of the balloon catheter to create a larger flow passage in the stenosis, deflating the balloon of the balloon catheter and removing the balloon catheter and the balloon-on-a-wire catheter from the stenosis.

2. A method as in claim 1 further comprising the step of passing the balloon of the balloon catheter over the balloon of the balloon-on-a-wire catheter while the balloon of the balloon-on-a-wire catheter is still in place in the stenosis.

3. A method as in claim 2 further comprising the steps of deflating the balloon on the balloon-on-a-wire catheter and advancing the balloon-on-a-wire catheter so that the balloon on the balloon-on-a-wire catheter is disposed distally of the stenosis prior to the time that the balloon of the balloon catheter is advanced over the balloon-on-a-wire catheter into the stenosis.

4. A method as in claim 3 further comprising the step of withdrawing the balloon catheter from the stenosis and introducing another balloon catheter having a larger size balloon thereon than the first named balloon catheter into the stenosis and inflating the balloon on the another balloon catheter to still further enlarge the flow passage through the stenosis.

5. A method for supplying apparatus performing an angioplasty procedure to a prospective user, providing a balloon-on-a-wire catheter having a proximal extremity with a lumen therein free of obstructions thereon and a distal extremity with a balloon thereon, the proximal extremity having a side opening therein in communication with the lumen, supplying a kit separate from the balloon-on-a-wire catheter including removable inflation means with first and second spaced-apart high pressure seals adapted to be placed over the proximal extremity of the balloon-on-a-wire catheter with the first and second high pressure seals being disposed on opposite sides of the side opening and thereby placed in communication with the lumen and removably secured thereto but making the high pressure seals with the balloon-on-a-wire catheter so that the balloon on the distal extremity on the balloon-on-a-wire catheter can be inflated and deflated through the inflation means.

6. A method as in claim 5 further comprising steps of providing a torquer in the kit, the torquer being adapted to be mounted on the proximal extremity of the balloon-on-a-wire catheter to apply a torque to the proximal extremity of the balloon-on-a-wire catheter.

7. A method as in claim 5 further comprising the step of supplying an introducer in the kit to be utilized in aiding insertion of the balloon-on-a-wire catheter into a guide catheter.

8. A method for performing an angioplasty procedure for treating one or more stenoses in a blood vessel and branches thereof of a patient by the use of a low profile balloon-on-a-wire catheter having a flexible elongate tubular member with proximal and distal extremities and with a balloon inflation/deflation lumen extending from the proximal extremity to the distal extremity, an inflatable balloon carried by the distal extremity of the flexible elongate tubular member, means carried by the flexible elongate tubular member for establishing communication between the lumen and the interior of the balloon and removable inflation means removably secured to the proximal extremity of the flexible elongate tubular member for supplying an inflation fluid to the lumen for inflating and deflating the balloon, the method comprising the steps of inserting the balloon-on-a-wire catheter into the vessel so that the balloon is disposed in a selected stenosis in the vessel, placing the removable inflation means on the proximal extremity of the flexible elongate tubular member so that it is in communication with the lumen, inflating the balloon to create an enlarged flow passage through the selected stenosis, removing the inflation means removably secured to the proximal extremity of the flexible elongate tubular member, introducing a balloon catheter over the flexible elongate tubular member utilizing the flexible elongate tubular member as a stand-alone guide wire for guiding the balloon of the balloon catheter into the selected stenosis while the balloon of the balloon-on-a-wire catheter is deflated, inflating the balloon of the balloon catheter to create a larger flow passage in the stenosis, deflating the balloon of the balloon catheter and removing the balloon catheter, redeploying the balloon-on-a-wire catheter so that the balloon thereon is in registration with another stenosis, placing the removable inflation means on the proximal extremity of the flexible elongate tubular member so that it is in communication with the lumen, inflating the balloon on the balloon-on-a-wire catheter to create an enlarged flow passage through the another stenosis, removing the inflation means removably secured to the proximal extremity of the flexible elongate tubular member, introducing a balloon catheter over the flexible elongate tubular member utilizing the flexible elongate tubular member as a stand-alone guide wire for guiding the balloon of the balloon catheter into the another stenosis while the balloon of the balloon-on-a-wire catheter is deflated, inflating the balloon of the balloon catheter to create a larger flow passage in the another stenosis, deflating the balloon of the balloon catheter and removing the balloon catheter and the balloon-on-a-wire catheter from the another stenosis.

* * * * *